US00PP17462P3

(12) United States Plant Patent
Fischer-Töhl

(10) Patent No.: US PP17,462 P3
(45) Date of Patent: Mar. 6, 2007

(54) ***GERANIUM* PLANT NAMED 'SIL RUBEN'**

(50) Latin Name: *Pelargonium peltatum*
Varietal Denomination: SIL RUBEN

(75) Inventor: Ilse Fischer-Töhl, Kirchlinteln (DE)

(73) Assignee: Silze GmbH & Company KG (DE)

( * ) Notice: Subject to any disclaimer, the term of this patent is extended or adjusted under 35 U.S.C. 154(b) by 151 days.

(21) Appl. No.: 11/017,582

(22) Filed: Dec. 20, 2004

(65) Prior Publication Data

US 2006/0137064 P1 Jun. 22, 2006

(51) Int. Cl.
*A01H 5/00* (2006.01)

(52) U.S. Cl. ..... Plt./332
(58) Field of Classification Search ..... Plt./332
See application file for complete search history.

(56) References Cited

U.S. PATENT DOCUMENTS

PP12,367 P2 * 1/2002 Utecht ..... Plt./332

OTHER PUBLICATIONS

UPOV ROM GTITM Computer Database, GTI Jouve Retrieval Software 2005/03, Citation for 'Sil Ruben'.*

European Plant Breeders Rights Application for 'Sil Ruben' filed Jun. 29, 2001, which was granted on Feb. 24, 2003 as Application No. EU 10625 and thereafter published on Apr. 15, 2003.

Toscana 2004/2005 catalog (May 2004).

Ball FloraPlant 2006 catalog p. 31 published in Mar. 2005.

Canadian Plant Breeders Right Application for 'Sil Ruben' filed on Feb. 18, 2005 and assigned Application No. 05–4605.

* cited by examiner

*Primary Examiner*—Wendy Haas
(74) *Attorney, Agent, or Firm*—Wood, Phillips, Katz, Clark & Mortimer

(57) ABSTRACT

A new and distinct cultivar of *Geranium* plant named 'SIL RUBEN' characterized by its large, semi-double dark red-colored flowers, medium green-colored foliage, freely branching character, and vigorous, mounded, and trailing growth habit.

2 Drawing Sheets

Latin name of genus and species of plant claimed: *Pelargonium peltatum.*
Variety denomination: 'SIL RUBEN'.

BACKGROUND OF THE INVENTION

The present invention relates to a new and distinct cultivar of *Geranium* plant botanically known as *Pelargonium peltatum* and hereinafter referred to by the cultivar name 'SIL RUBEN'.

The new cultivar originated in a controlled breeding program in Weener, Germany, during summer 1998. The objective of the breeding program was the development of *Geranium* cultivars with a vigorous, mounded, and trailing growth habit, freely branching character, medium green-colored foliage, and new and unique flower color.

The new cultivar originated from the open pollination of 'PENRO', not patented, characterized by its medium sized, bright red-colored flowers. The pollen was derived from a mix of red flowering Ivy *Geraniums*. The new *Geranium* was discovered and selected by the inventor as a single flowering plant within the progeny of the above stated open-pollination during June 1999 at Weener, Germany.

Asexual reproduction of the new cultivar by terminal stem cuttings taken since June 1999 at Weener, Germany, has demonstrated that the new cultivar reproduces true to type with all characteristics, as herein described, firmly fixed and retained through successive generations of such asexual propagation.

SUMMARY OF THE INVENTION

The following characteristics of the new cultivar have been repeatedly observed and can be used to distinguish 'SIL RUBEN' as a new and distinct cultivar of *Geranium* plant:

1. Large, semi-double dark red-colored flowers.
2. Medium green-colored foliage.
3. Freely branching.
4. Vigorous, mounded, and trailing growth habit.

Plants of the new cultivar differ from plants of the female primarily in growth habit and flower size.

Of the many commercially available *Geranium* cultivars known to the inventor, the most similar in comparison to the new cultivar is 'Fisbarock', U.S. Plant Pat. No. 12,367. However, in side by side comparisons, plants of the new cultivar differ from plants of 'Fisbarock' in the following characteristics:

1. Plants of the new cultivar have fewer petals per floret than plants of 'Fisbarock'.
2. Plants of the new cultivar have fewer florets per umbel than plants of 'Fisbarock'.

BRIEF DESCRIPTION OF THE PHOTOGRAPHS

The accompanying photographs show, as nearly true as it is reasonably possible to make the same in color illustrations of this type, typical flower and foliage characteristics of the new cultivar. Colors in the photographs differ slightly from the color values cited in the detailed description which accurately describes the colors of 'SIL RUBEN'. The plants were grown in a greenhouse at West Chicago, Ill.

DETAILED BOTANICAL DESCRIPTION

Figure 1:
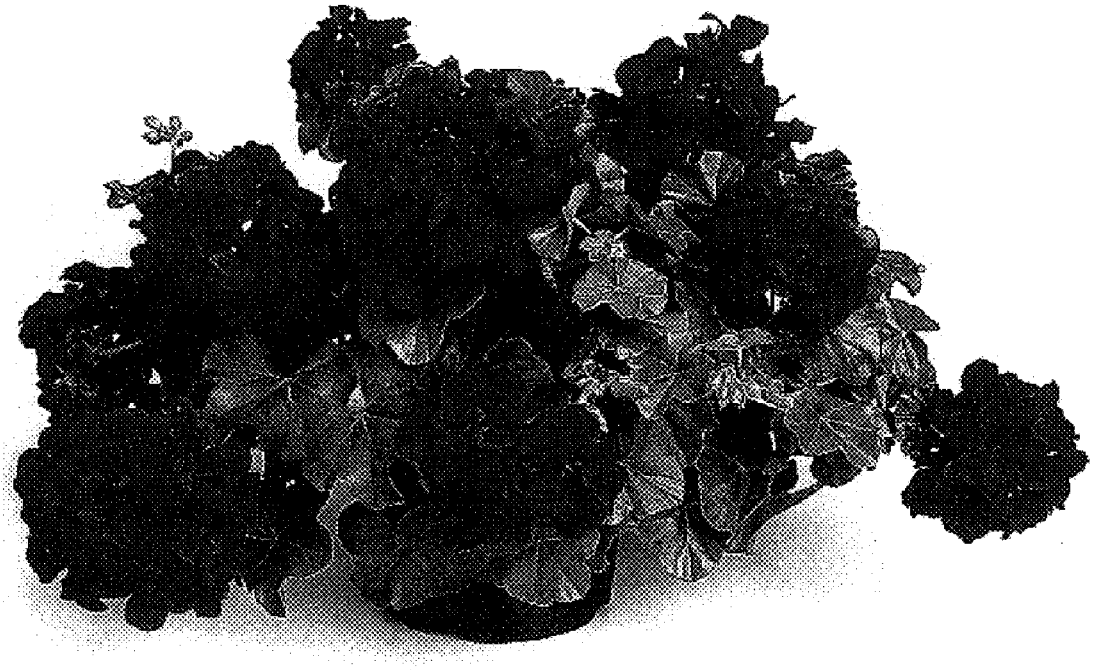
FIG. 1 illustrates a side view of the overall growth and flowering habit of 'SIL RUBEN' grown for 10 weeks with three plants in a 16 cm pot.
Figure 2:
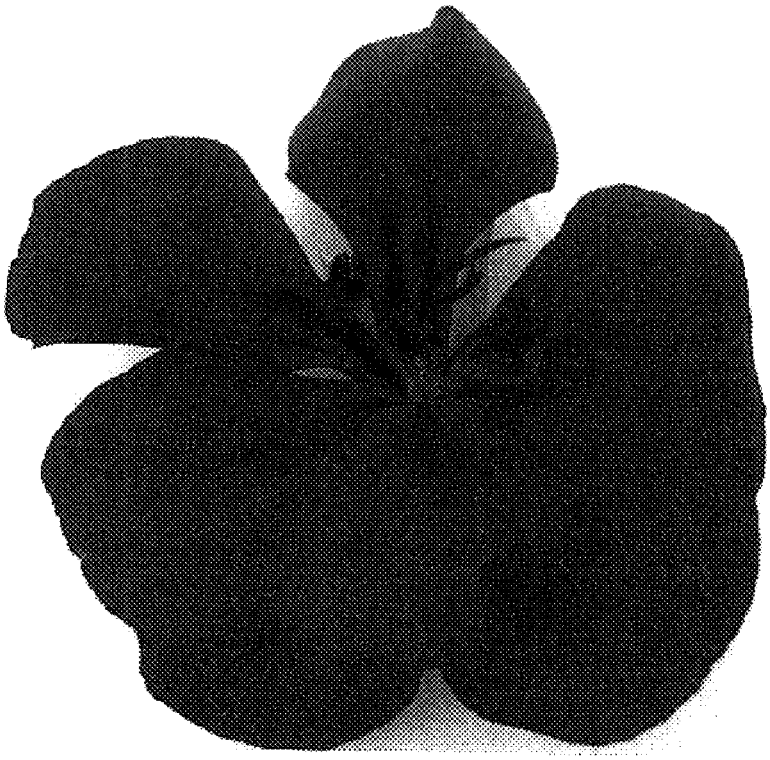
FIG. 2 illustrates a close-up view of a single flower of 'SIL RUBEN'.
Figure 3:
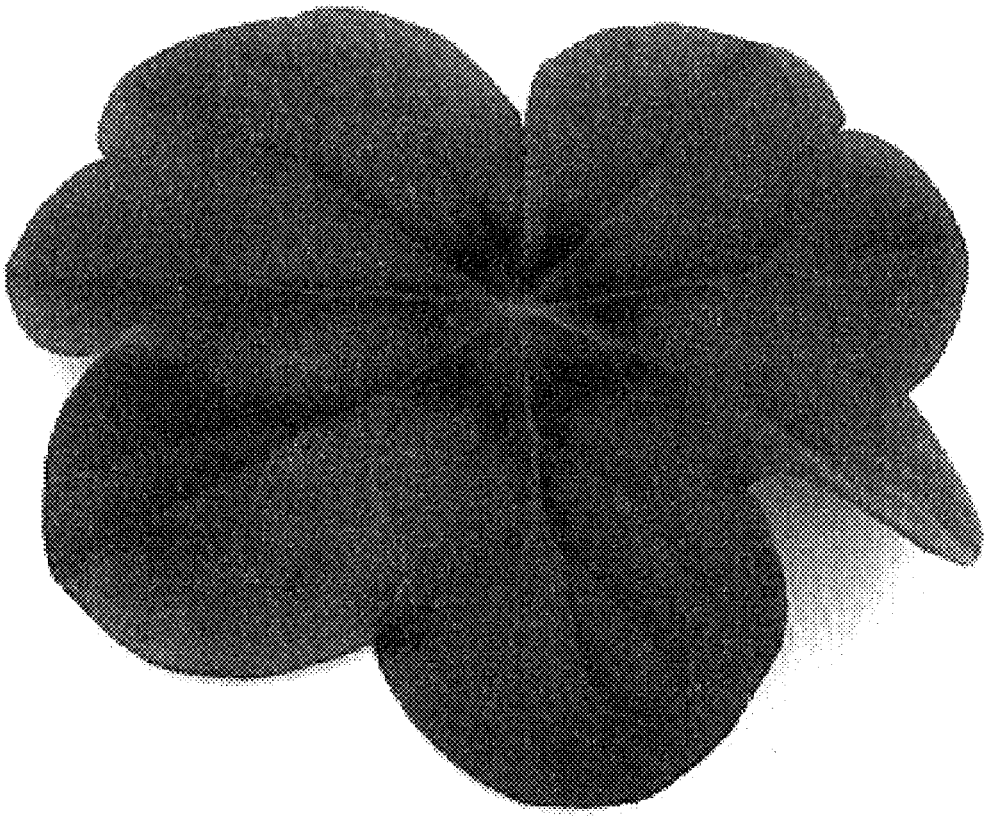

The new cultivar has not been observed under all possible environmental conditions to date. Accordingly, it is possible that the phenotype may vary somewhat with variations in the environment, such as temperature, light intensity, and day length, without, however, any variance in genotype.

The chart used in the identification of colors described herein is The R.H.S Colour Chart of The Royal Horticultural Society, London, England, 2001 edition, except where general color terms of ordinary significance are used. The color values were determined on Sep. 9, 2004 between 4:00 and 5:00 p.m. under natural light conditions, in Arroyo Grande, Calif.

The following descriptions and measurements describe plants produced from cuttings taken from stock plants and grown in a double polycarbonate-covered greenhouse under conditions comparable to those used in commercial practice. The plants were grown at Arroyo Grande, Calif. in 10 cm pots for 10 weeks utilizing a soilless growth medium. Greenhouse temperatures were maintained at approximately 65° F. to 70° F. (18° C. to 21° C.) during the day and approximately 60° F. to 65° F. (15° C. to 18° C.) during the night. Greenhouse light levels of 4,000 to 6,000 footcandles were maintained during the day.

Botanical classification: *Pelargonium peltatum* cultivar SIL RUBEN.

Parentage: Pollination of 'PENRO' with a mix of pollen from red flowering Ivy *Geraniums.*

Propagation:

*Type cutting.*—Terminal stem.

*Time to initiate roots.*—Approximately 10 to 14 days.

*Time to produce a rooted cutting.*—Approximately 21 to 28 days.

*Root description.*—Fibrous.

*Rooting habit.*—Freely branching.

Plant description:

*Crop time.*—Approximately 8 weeks from a rooted cutting to finish in a 10 cm pot.

*Growth habit and general appearance.*—Vigorous, mounded, and trailing.

*Height from soil level to top of plant plane.*—Approximately 36.5 cm.

*Width/area of spread.*—Approximately 49.5 cm.

*Branching habit.*—Freely basal branching. Approximately 4 branches per plant.

*Branch description.*—Strength: Strong. Length: Approximately 26.3 cm. Diameter: Approximately 4.3 mm. Texture: Pubescent. Color: 146B. Internode length at center of branch: Approximately 4.1 cm.

*Foliage description.*—Number of leaves per lateral branch: Approximately 10. Fragrance: None. Form: Mature foliage is simple. Arrangement: Opposite. Shape: Peltate. Margin: Crenate. Apex: Rounded. Base: Cordate. Venation pattern: Palmate. Texture of upper surface: Densely pubescent. Texture of lower surface: Glabrous. Color of upper surface of mature foliage: Slightly lighter than 147A. Color of lower surface of mature foliage: Closest to 147B. Length of mature leaf: Approximately 4.2 cm. Width of mature leaf: Approximately 7.5 cm. Petiole length: Approximately 4.2 cm. Petiole diameter: Approximately 2 mm. Petiole Texture: Pubescent on both upper and lower surface. Petiole color: 146B.

Flowering description:

*Outdoor flowering habit.*—'SIL RUBEN' is freely flowering under outdoor growing conditions with substantially continuous blooming from spring through autumn and year round in greenhouse environment.

*Time to first flower.*—Approximately 8 weeks after planting of rooted cutting.

*Lastingness of individual bloom.*—Approximately 5 to 7 days.

Inflorescence description:

*Type.*—Hemispherical umbel. Position: Above foliage. Number of open umbels at any one time: Approximately 3. Number of developing umbels at any one time: Approximately 2. Diameter of fully open umbel: Approximately 8 cm. Height/depth of fully open umbel: Approximately 6.9 cm. Number of flowers per umbel: Approximately 7.

*Peduncle.*—Strong, erect. Length: Approximately 14.6 cm. Diameter: Approximately 3 mm. Texture: Pubescent. Color: 144A.

Flower description:

*Bud just before opening.*—Shape: Elliptic. Length: Approximately 1.5 cm. Diameter: Approximately 7.5 mm. Texture of sepals: Dense. Petal color: Closest to but darker than 53A. Sepal color: N144C.

*Corolla.*—Form: Semi-double. Shape: Round, slightly cupped. Diameter/Width: Approximately 5.3 cm. Depth: Approximately 2.4 cm. Fragrance: None.

*Petals/petaloids.*—Quantity: Approximately 7 petals and 4 petaloids per flower. Arrangement: Imbricate. Shape: Obovate. Apex: Obtuse. Base: Attenuate. Margin: Entire. Texture of upper and lower surface: Glabrous. Upper petal length: Approximately 3.3 cm. Upper petal width: Approximately 2 cm. Lower petal length: Approximately 2.7 cm. Lower petal width: Approximately 2 cm. Color of upper surface of fully open upper petals: Closest to 53B with venation of 187A. Color of upper surface of fully open lower petals: Closest to 53B. Color of lower surface of fully open upper petals: Lighter and brighter than 53A. Color of lower surface of fully open lower petals: Lighter and brighter than 53A.

*Pedicel.*—Strength: Strong. Angle: Acute. Length: Approximately 2.6 cm. Diameter: Approximately 1.3 mm. Texture: Pubescent. Color: 144B with overlay of 183B in mid-section.

*Sepals.*—Quantity per flower: 5. Shape: Lanceolate. Tip: Acuminate. Base: Truncate. Margin: Entire. Length of largest sepal: 1.6 cm. Width of largest sepal: 5 mm. Length of smallest sepal: 1.2 cm. Width of smallest sepal: 1.2 mm. Texture: Upper/inner surface: Puberulent at apex, glabrous at base. Lower/outer surface: Pubescent. Color: Upper and lower surface: 143B.

*Reproductive organs.*—Androecium: 6 fertile anthers per flower. Anther length: Approximately 3 mm. Anther color: N92B. Filament color: 56A. Pollen amount: Moderate. Pollen color: 26A. Gynoecium:

Pistil quantity: One per flower. Pistil length: Approximately 1.5 cm. Stigma shape: 5 lobed. Stigma length: 5 mm. Stigma color: 59A. Style length: 4 mm. Style color: N155D. Ovary length: 6 mm. Ovary diameter: 2 mm. Ovary texture: Sericeous. Ovary color: 144A.

Seed and fruit production: Neither seed nor fruit production has been observed.

Disease and pest resistance: Resistance to pathogens and pests common to *geraniums* has not been observed.

What is claimed:

1. A new and distinct cultivar of *Geranium* plant named 'SIL RUBEN', substantially as herein shown and described.

* * * * *